United States Patent [19]

Madaus et al.

[11] 3,998,964
[45] Dec. 21, 1976

[54] α-AMINO-β-(N-BENZYLTHIOCARBAM-OYLTHIO) PROPIONIC ACID AND THERAPEUTIC COMPOSITIONS

[75] Inventors: Rolf Madaus, Cologne-Bruck; Gerhard Brüsewitz, Bensberg, both of Germany

[73] Assignee: Dr. Madaus & Co., Cologne, Germany

[22] Filed: Feb. 4, 1974

[21] Appl. No.: 438,975

Related U.S. Application Data

[63] Continuation of Ser. No. 173,673, Aug. 20, 1971, abandoned.

[30] Foreign Application Priority Data

Aug. 22, 1970 Germany .......................... 2041831

[52] U.S. Cl. ........................ 424/300; 260/455 A
[51] Int. Cl.$^2$ ................ A61K 31/27; C07C 155/08
[58] Field of Search ................ 260/455 A; 424/300

[56] References Cited

UNITED STATES PATENTS

| 2,325,720 | 8/1943 | Vrbschat et al. ................... 424/300 |
|-----------|--------|---------------------------------------------|
| 2,621,143 | 12/1952 | Goodhue et al. ................... 424/300 |
| 2,650,876 | 9/1953 | Stewart ............................. 424/300 |
| 2,885,433 | 5/1959 | Hagemann et al. ................ 424/300 |
| 3,089,887 | 5/1963 | Metivier ......................... 260/455 A |
| 3,133,112 | 5/1964 | Shive et al. ..................... 260/455 A |
| 3,539,612 | 11/1970 | Tweit ............................. 260/455 A |

OTHER PUBLICATIONS

Plijgers et al., "Syn. and Antifungal Activity etc.," (1967), Index Chemicas 33, No. 114, 196 (1969).
Smith et al., "Biol—Activities of Some Amino Acid etc.," (1962), Tex. Rpt. Biol. Med. Bd. 21, pp. 296–301, (1963).

Primary Examiner—Lewis Gotts
Assistant Examiner—D. R. Phillips
Attorney, Agent, or Firm—Burgess, Dinklage & Sprung

[57] ABSTRACT

α-Amino-β-(N-benzylthiocarbamoylthio)propionic acid provides strong anti-bacterial and anti-mycotic action coupled with excellent stability and tolerability when administered orally in mustard oil therapy.

15 Claims, No Drawings

α-AMINO-β-(N-BENZYLTHIOCARBAMOYLTHIO) PROPIONIC ACID AND THERAPEUTIC COMPOSITIONS

This is a continuation of application Ser. No. 173,673, filed Aug. 20, 1971, now abandoned.

This invention relates to a new chemical compound and to pharmaceutical compositions containing it, more specifically to compositions enabling oral mustard oil therapy.

It has so far been possible to make only limited use of the known good antibacterial and antimycotic effect of mustard oils for therapeutic purposes, because, owing to the fact that free mustard oil irritates the mucous membranes and is badly tolerated, a therapeutically adequate dosage cannot be taken, even if it is given in capsule form in order to prevent upset to the senses of smell and taste, and to protect the stomach.

Similarly, the oral use of mustard oil glycosides, from which mustard oil is formed by the action of the enzyme, nyrosinase, or of the synthetic substances known as mustard oil formers, has proved to be unsuitable, because the mustard oils are released either at an unsuitable place, or not at all, or are broken down and metabolized, without reaching the areas of intended effectiveness in the necessary concentration. Furthermore, harmful cleavage products are often formed when the oil is released.

It has now been found that a novel compound, viz. α-amino-β-propionic acid, possesses exceptional therapeutic properties in terms of strong antibacterial and antimycotic action coupled with excellent stability and tolerability when administered orally.

The compound of this invention has the following structural formula:

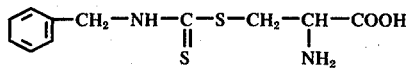

and a melting range of between 187°C and 190°C. This compound has been named α-amino-β-[(N-benzylthiocarbamoyl)-thiol]proprionic acid, in accordance with I.U.P.A.C. nomenclature, but can also be referred to as N-benzyl(α-aminopropionic acid)dithiocarbamic acid ester.

This ester is a white, powdery substance with a slight smell peculiar to the dithiocarbamic acid ester compounds. It is very difficult to dissolve in water and is more easily soluble in dilute hydrochloric acid. In an acid medium, the ester remains stable, but in an alkaline one it appears to separate hydrolytically into benzyl mustard oil and cysteine.

These properties are advantageous with regard to stability, tolerability and oral medication.

When the ester is given by mouth, it is dissolved and dispersed in the stomach, but apparently is not cleaved, so that there is no possibility of irritation of the gastric mucosa.

Clinically, the ester was administered in doses of 2 dragrees 3 to 4 times daily, each containing 60 mg of active substance, and a good degree of success was achieved in acute and chronic pyelonephritis, pyelocystitis, cystitis, unrethritis, epididymitis; and in yeast infections.

In comparative clinical tests of tolerance, in which 340 patients were involved (among them 50 children and 60 suffering from skin diseases) with infections of the urinary tract, chronic and acute pyelonephritis, and various disorders of the male adnexa, with accompanying infection, 9 testers were in general agreement that tolerance was far better than to pure benzyl mustard oil, given in the form of stomach-resistant capsules, although the unit of dosage was more than doubled (from 14 to 32 mg, as compared with benzyl mustard oil). For a period of up to several weeks, dosages ranging from one 60 mg-dragee twice daily (children) to 2 dragees 4 times daily, were given. The infections involved comprised 290 caused by bacteria, and 50 caused by saccharomyces.

The compound of this invention can be prepared by the reaction of benzyl isothiocyanate with L(+)-cysteine, preferably in a solvent medium. It has been found important, in order to prevent the unwanted formation of a closed ring compound, to carry out the above reaction in a neutral medium.

Advantageously, an aqueous solution of cysteine, and, in an equimolar ratio, an 80%, alcohol solution of mustard oil are prepared, and the two solutions are combined while being stirred, and then left to stand for 2 to 3 days, with occasional stirring, at room temperature. After removal of the supernatant by filtration under suction, the precipitated dithiocarbamic acid ester is washed, first with distilled water and then with alcohol, and dried at 50° to 60°C.

Instead of cysteine, 1.45 times the quantity of L(+)-cysteine-hydrochloride-monohydrate can also be used with advantage, if this quantity is dissolved in 3.5 times the amount of water, in which 6.6% sodium hydroxide has previously been dissolved.

By virtue of its good solubility in water, the use of the hydrochloride has the advantage, with regard to large-scale manufacture, that it is possible to work with relatively small quantities of solvent. Furthermore, the conversion of the hydrochloride, in the presence of the alkali hydroxide, is accomplished particularly smoothly, as it were in statu nascendi.

EXAMPLE 1.

Preparation of α-amino-β-[(N-benzylthiocarbamoyl)-thio]propionic acid 1.52 kg 12.5 moles) L(+)-cysteine were dissolved in 52 l of distilled water and, while being vigorously stirred, added, at room temperature, to a solution consisting of 1.72 kg (11.5 moles) of rectified benzyl isothiocyanate in 40 l of 80% ethanol denatured with methyl-ethyl-ketone.

After the solution had stood for 48 hours, at room temperature, with occasional stirring, the process of conversion was almost complete.

The supernatant was then removed by suction and the precipitated product was washed twice with distilled water to remove any non-converted cysteine, and then twice with ethanol to remove any non-converted benzyl isothiocyanate. The product was dried in the vacuum drying chamber at 50° to 60°C.

The colorless product which was obtained, N-benzyl-(α-aminopropionic acid)-dithicarbamic acid ester or α-amino-β-[(N-benzylthiocarbamoyl)-thio] propionic acid, can be crystallized from water which has been slightly acidified with hydrochloric acid.

Yield: 2.35 kg = 72.5% (theoretical)

Melting range: 187° to 190°C

The structure was confirmed by NMR spectra and IR spectra and the presence of the free $NH_2$-group was further established by filtration with glacial acetic acid/perchloric acid.

EXAMPLE 2.

Preparation using cysteine hydrochloride 1.16 kg (6.6 moles) L(+)-cysteine -hydrochloride-monohydrate (corresponding to 0.8 kg of cysteine) were stirred into 4 l of distilled water, in which 0.264 kg of sodium hydroxide had previously been dissolved. 0.990 kg (6.6 moles) of rectified benzyl isothiocyanate were dissolved in 25 l of 30% ethanol denatured with methyl ethyl-ketone. This ethanol benzyl isothiocyanate solution was added, with vigorous stirring, to the aqueous cysteine solution at room temperature. In the process, the reaction product was precipitated immediately. The deposit was left to stand for 2 to 3 days at room temperature, with occasional stirring. At the end of this time, the conversion process was almost complete.

The reaction product which had been formed was subjected to the further treatment described in Example 1.

Yield 1.8 kg = 83.5% (theoretical)
Melting range: 187° to 190° C.

EXAMPLE 3.

Preparation of therapeutic tablets 6 kg of N-benzyl-($\alpha$-aminopropionic acid)- dithiocarbamic acid ester were mixed with 18.75 kg of lactose and 0.25 kg of magnesium stearate, and compressed into tablets, each weighing 0.25 g (content of active substance 60 mg).

The compressed tablets can be used as such, or as the nucleus for the preparation of dragees, by using 20 kg of the usual constituents, so that dragees weighing about 0.45 g are produced.

It will be understood that the specification and examples are illustrative but not limitative of the present invention and that other embodiments within the spirit and scope of the invention will suggest themselves to those skilled in the art.

what is claimed is:

1. $\alpha$-Amino-$\beta$-[(N-benzylthiocarbamoyl)-thio] propionic acid.

2. In a process for preparing $\alpha$- amino-$\beta$-[(N-benzylthiocarbamoyl)-thio] propionic acid as claimed in claim 1, which process comprises contacting cysteine with benzyl isothiocyanate in about equimolar ratio, the improvement comprising conducting said contacting in a substantially neutral, at least partly aqueous, medium, mixing the reaction mixture vigorously and maintaining the mixture at room temperature for 2 to 3 days, and recovering the resultant precipitate containing the said $\alpha$-amino-$\beta$-[(N-benzylthiocarbamoyl)-thio] propionic acid.

3. Process as claimed in claim 2 wherein the said cysteine is supplied in the form of L(+)-cysteine- hydrochloride-monohydrate in an amount 1.45 per mole of benzyl isothiocyanate, said monohydrate being dissolved in water containing alkalihydroxide.

4. Process as claimed in claim 2, wherein said cysteine is supplied in the form of an aqueous solution thereof and the benzyl isothiocyanate is in the form of an alcohol solution thereof.

5. Process as claimed in claim 4, wherein the said alcohol solution of benzyl isothiocyanate is a substantially 80% alcohol solution.

6. Process as claimed in claim 2, wherein said cysteine is supplied in slight molar excess to said benzyl isothiocyanate.

7. Process as claimed in claim 2, wherein the cysteine is in the form of an aqueous solution thereof, the benzyl isothiocyanate is in the form of an alcohol solution thereof, and the cysteine is in slight molar excess to the benzyl isothiocyanate.

8. Process as claimed in claim 7, wherein the mole ratio of cysteine to benzyl isothiocyanate is about 1.1 to 1.

9. Therapeutic composition for the oral treatment of bacterial and mycotic disorders comprising a pharmaceutically acceptable carrier and as an active ingredient $\alpha$-amino-$\beta$- [(N-benzylthiocarbamoyl)-thio] propionic acid as claimed in claim 1, in therapeutically effective amounts.

10. Composition as claimed in claim 9, in the form of a tablet or dragee containing from 50 to 100 milligrams of said $\alpha$-amino-$\beta$-[(N-benzylthiocarbamoyl)- thio]propionic acid.

11. Composition as claimed in claim 10 wherein said tablet or dragee is about 0.5 grams in weight.

12. Method of treating a subject against afflictions requiring antibacterial or antimycotic action which comprises administering to said subject in therapeutically effective amounts $\alpha$-amino-$\beta$-[(N-benzylthiocarbamoyl)- thio]propionic acid.

13. Method as claimed in claim 12 wherein said $\alpha$-amino-$\beta$-[(N-benzylthiocarbamoyl)-thio]propionic acid is administered orally.

14. Method as claimed in claim 12 wherein said $\alpha$-amino-$\beta$-[(N-benzylthiocarbamoyl)-thio]propionic acid is administered in the form of a tablet or dragee containing from about 50 to 100 milligrams of said acid.

15. Method as claimed in claim 14 wherein such tablets or dragees are administered at a dosage of two tablets or dragees 3 to 4 times daily.

* * * * *